(12) United States Patent
Liao et al.

(10) Patent No.: US 8,712,177 B2
(45) Date of Patent: Apr. 29, 2014

(54) MOTION COMPENSATED OVERLAY

(75) Inventors: Rui Liao, Princeton Junction, NJ (US);
Yefeng Zheng, Dayton, NJ (US);
Matthias John, Nürnberg (DE); Alois Nöttling, Pottenstein (DE); Jan Boese, Eckental (DE)

(73) Assignee: Siemens Aktiengesellschaft, Munich (DE)

( * ) Notice: Subject to any disclaimer, the term of this patent is extended or adjusted under 35 U.S.C. 154(b) by 0 days.

(21) Appl. No.: 13/348,879

(22) Filed: Jan. 12, 2012

(65) Prior Publication Data

US 2013/0279825 A1 Oct. 24, 2013

Related U.S. Application Data

(60) Provisional application No. 61/435,888, filed on Jan. 25, 2011.

(51) Int. Cl.
*G06K 9/36* (2006.01)
(52) U.S. Cl.
USPC .......................................................... 382/254
(58) Field of Classification Search
None
See application file for complete search history.

(56) References Cited

U.S. PATENT DOCUMENTS

| | | | | |
|---|---|---|---|---|
| 6,782,287 | B2 * | 8/2004 | Grzeszczuk et al. | 600/424 |
| 7,664,542 | B2 * | 2/2010 | Boese et al. | 600/411 |
| 7,756,567 | B2 * | 7/2010 | Kuduvalli et al. | 600/427 |
| 8,150,495 | B2 * | 4/2012 | Edwards et al. | 600/424 |
| 2007/0238952 | A1 * | 10/2007 | Boese et al. | 600/407 |
| 2008/0267490 | A1 * | 10/2008 | Gorges et al. | 382/154 |
| 2009/0088634 | A1 * | 4/2009 | Zhao et al. | 600/427 |
| 2009/0281566 | A1 * | 11/2009 | Edwards et al. | 606/214 |
| 2010/0157041 | A1 * | 6/2010 | Klaiman et al. | 348/77 |
| 2012/0230565 | A1 * | 9/2012 | Steinberg et al. | 382/130 |

OTHER PUBLICATIONS

Zarkh et al., "Guide wire navigation and therapeutic device localization for catheterization procedure", International Congress Series 1281 (2005) 311-316.*

* cited by examiner

*Primary Examiner* — Bhavesh Mehta
*Assistant Examiner* — Feng Niu
(74) *Attorney, Agent, or Firm* — Donald B. Paschburg; F. Chau & Associates, LLC

(57) ABSTRACT

A method for displaying a motion compensated overlay includes receiving a model of a structure of interest, capturing an image depicting a region of interest and an instrument, determining whether the structure of interest is visible in the image, registering the model of the structure of interest to the image upon determining that the structure of interest is visible, and combining the model of the structure of interest with the image according to a registration to determine an overlay image.

10 Claims, 3 Drawing Sheets

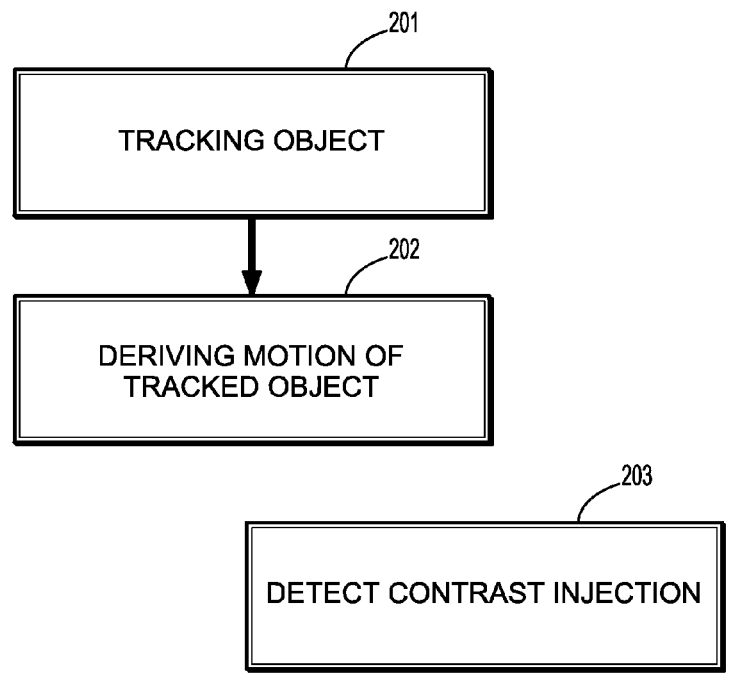
FIG. 2
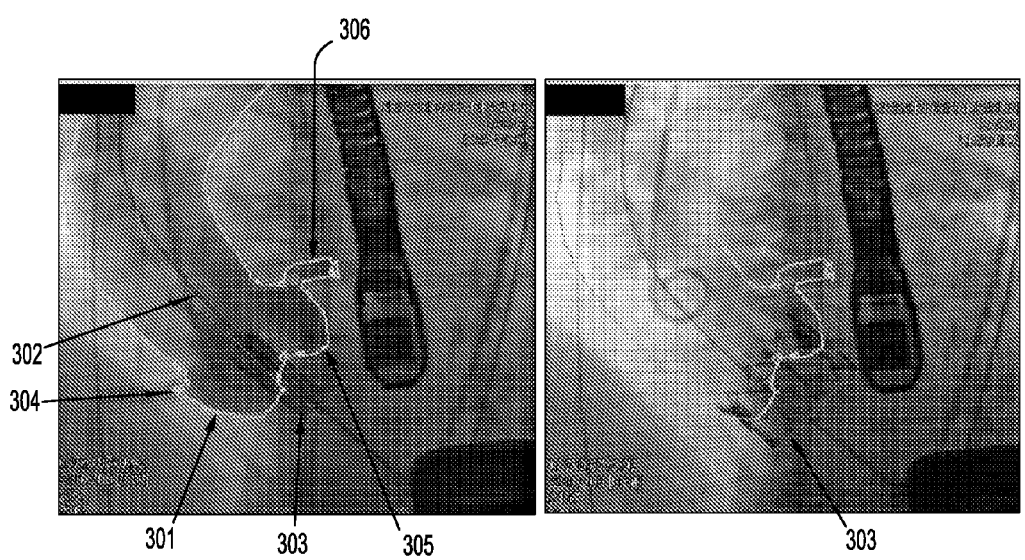
FIG. 3A  FIG. 3B

MOTION COMPENSATED OVERLAY

CROSS-REFERENCE TO RELATED APPLICATION

This is a non-provisional application claiming the benefit of U.S. provisional application Ser. No. 61/435,888, filed Jan. 25, 2011, the contents of which are herein incorporated by reference in their entirety.

BACKGROUND

1. Technical Field

The present disclosure relates to overlay of image data, and more particularly to motion compensated overlays.

2. Discussion of Related Art

Transcatheter aortic valve implantation (TAVI) is a hybrid operating-room procedure that is typically performed in high-risk patients (e.g., patients older than 80 years) with aortic valve defects. TAVI is considered to be an alternative to conventional open-heart surgical techniques that need sternotomy with extracorporeal circulation and cardioplegic cardiac arrest. In either case, implantation of a prosthetic aortic valve is often needed to replace the severely damaged native valve. Though open-chest valve surgery is a well-established procedure, TAVI may be used, particularly for high-risk patients.

BRIEF SUMMARY

According to an embodiment of the present disclosure, a method for displaying a motion compensated overlay includes receiving a model of a structure of interest, capturing an image depicting a region of interest and an instrument, determining whether the structure of interest is visible in the image, registering the model of the structure of interest to the image upon determining that the structure of interest is visible, and combining the model of the structure of interest with the image according to a registration to determine an overlay image.

According to an exemplary embodiment of the present disclosure, a method further comprises determining a relative position of the model of the structure of interest and the instrument in the overlay image.

According to an exemplary embodiment of the present disclosure, an image is of a live fluoroscopic scene.

According to an exemplary embodiment of the present disclosure, a method includes detecting a contrast agent in the live fluoroscopic scene.

According to an exemplary embodiment of the present disclosure, a method includes tracking the structure of interest or the instrument in the image, and deriving a motion of the structure of interest or the instrument from the tracking, wherein the registration of the model of the structure of interest to the image is performed in real-time.

According to an exemplary embodiment, a model is a silhouette view of the structure of interest.

According to an exemplary embodiment of the present disclosure, a computer program product embodies instructions executable by a processor to perform a method for displaying a motion compensated overlay.

According to an exemplary embodiment of the present disclosure, a method for displaying a motion compensated overlay includes receiving a model of a structure of interest, capturing an image depicting a region of interest and an instrument, determining whether the structure of interest is visible in the image, determining a position of the instrument in the image upon determining that the structure of interest is not visible, and combining the model and the image relative to the position of the instrument to determine an overlay image.

According to an exemplary embodiment of the present disclosure, a method includes determining the position of the instrument in the image further comprises retrieving a previously determined position of the instrument relative to the model in a previous image and applying the previously determined position of the position of the instrument in the image.

According to an exemplary embodiment of the present disclosure, a method for displaying a motion compensated overlay includes receiving a model of a structure of interest, capturing an image depicting a region of interest, determining that neither a structure of interest nor an instrument is visible in the image, and generating an overlay image by combining the model with the image according to a position of the model determined in a previous image or combining the model with the image according to a position of the model estimated from a known motion of the structure of interest.

According to an exemplary embodiment of the present disclosure, a system for performing a method of displaying a motion compensated overlay includes a processor configured to determine an overlay including a model of a structure of interest and an image, wherein the processor executes instructions to perform a method including receiving the model of a structure of interest, capturing the image depicting a region of interest and an instrument, determining whether the structure of interest is visible in the image, registering the model of the structure of interest to the image upon determining that the structure of interest is visible, combining the model of the structure of interest with the image according to a registration to determine an overlay image, and determining a relative position of the model of the structure of interest and the instrument in the overlay image, and the system includes a memory configured to store the overlay image.

BRIEF DESCRIPTION OF THE DRAWINGS

Preferred embodiments of the present disclosure will be described below in more detail, with reference to the accompanying drawings:

FIG. 2 is a flow diagram for a live image application according to an exemplary embodiment of the present disclosure;

FIG. 3A is an exemplary image overlay with contrast injection into an aortic root according to an exemplary embodiment of the present disclosure;

FIG. 3B is an exemplary image overlay without contrast injection with a deployed valve prosthesis according to an exemplary embodiment of the present disclosure.

DETAILED DESCRIPTION OF PREFERRED EMBODIMENTS

Figure 1:
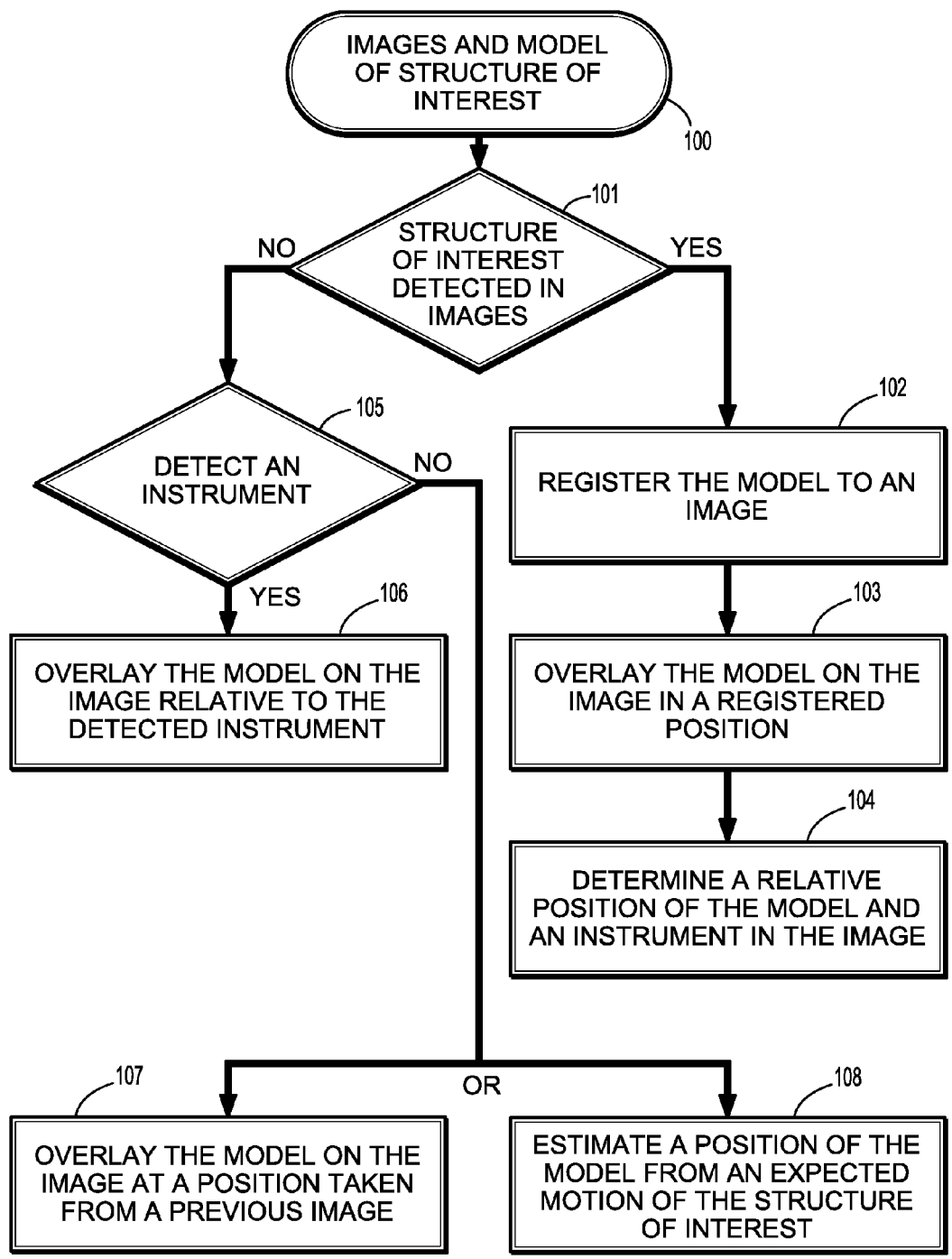
FIG. 1 is a flow diagram showing a method for model registration with motion compensated overlays according to an exemplary embodiment of the present disclosure.

According to an embodiment of the present disclosure, an overlay image derived from pre-operation data and/or annotated data may be extended for motion compensated overlay for 2D/3D image registration.

Exemplary embodiments of the present disclosure may be applied to reduce risks associated with various surgical procedures. For example, in the context of implantation or repair of a heart valve using two-dimensional (2D) X-ray guidance, embodiments of the present disclosure provide for the pre- or peri-operative three-dimensional (3D) imaging of a region of interest including a structure of interest (e.g., an aortic root in a cardiac image) and derivation of a 3D model from the 3D volumetric data.

In an exemplary case, transcatheter aortic valve implantation (TAVI), which is typically reserved for high-risk patients, may be applied in lower risk cases when coupled with an automatic 2D/3D image registration. During a TAVI procedure, an aortic valve prosthesis may be inserted via a catheter under X-ray guidance. To make an aortic root anatomy visible in X-ray images, contrast dye may be injected into the patient. Repeated contrast injections (e.g., 3 to 5) may be needed during the procedure in a time frame of about 15 to 30 minutes. In some cases, e.g., for patients suffering from renal impairment or those susceptible to nephrotoxicity, the amount of dye needs to be minimized.

Therefore, an improved guidance between the contrast injections may reduce the time needed to perform the procedure and reduce the amount of contrast dye used during the procedure.

According to an embodiment of the present disclosure, automated motion compensation may be used for model overlay (e.g., in X-ray and 3D datasets) by combining instrument tracking and model registration (e.g., 2D/3D image registration) for various surgical procedures, including TAVI. In one example, motion compensation in an overlay for aortic valve implantations may be achieved by adding an automatic registration of an overlaid model and an aimed target after each contrast injection.

To generate a 3D model of the aimed target derived from pre-operative 3D images that compensates for motion, available landmarks or features in the pre-operative 3D images may be used for tracking the motion of the aimed target. In an exemplary case of TAVI, one such landmark or feature is a pigtail catheter instrument, which is routinely used in TAVI procedures for injecting contrast agent and which is typically placed at the aortic root. Another landmark may be calcifications (i.e., hardened depositions of calcium salts) at the diseased valve and/or the proximal end of the coronary arteries. The pigtail catheter and the calcium deposits represent suitable objects to be tracked in order to estimate the motion of the aimed target or structure of interest in TAVI procedures. Other objects may also be used and incorporated into the framework if they are at a relatively fixed position and are not frequently moved with respect to the aimed target during the procedure, where motion comes mainly from cardiac and respiratory motion, or where movement due to cardiac and respiratory motion either closely represents, or is in a synchronized fashion, with the global motion of the aimed target (e.g., the structure of interest for motion compensation during TAVI procedures).

To guide the valve navigation and placement between contrast injections, the 3D model of the aimed target derived from pre-operative 3D images may be overlaid on the output of an imaging system (e.g., an X-ray system), achieving a 2D/3D image registration. In an exemplary case of a TAVI procedure, an aortic root may be considered the aimed target. According to an embodiment of the present disclosure, an overlay including the 3D model is moved with the aortic root of the patient as the aortic root moves during the TAVI procedure (e.g., due to cardiac motion, respiratory motion, instrument motion, etc.).

Referring to FIG. 1, for each acquired image (100) (e.g., X-ray fluoroscopic images), it is determined whether an aortic root is detected (101). If the aortic root is detected in the image, a previously determined 3D model of the aortic root may be registered to the image (102). For example, the aortic root shape and landmarks may be determined in the 3D volumetric data. A machine learning based algorithm may be used to detect the aortic root shape and some landmarks, in particular the lowest point of each aortic root cusps, the coronary artery ostia, the commissures points where the cusps meet, and the centerline. The position, orientation, and scale of the aortic root may be estimated using the landmarks. An exemplary, non-limiting method for doing these estimations is the Marginal Space Learning algorithm. The mean aortic root shape, which is determined from a training set, may be aligned with the estimated pose, followed by boundary refinement using a learning-based 3D boundary detector.

The 3D model may be combined with the image, such that the 3D model is overlaid on the image (103). The combined image including the 3D model may be displayed, wherein the 3D model is disposed in the registered position. More particularly, the 3D model or its silhouette may be rendered on the image to produce the combined image (see for example, a 3D aortic model 301 rendered in FIG. 3A). A relative position of the model position in the combined image to an instrument/structure position in the image or a neighboring image may be determined (104). The determination of relative position may output a distance measured in distance (e.g., millimeters), pixels, etc.

When overlaying the 3D model onto a live fluoroscopic scene, a silhouette view of the 3D model showing sufficient information for prosthesis positioning and deployment, but less than all of the available information, may be used. Therefore, less fluoroscopic image space is covered as compared to volume rendering, which yields improved fluoroscopic image quality in the overlay for implantation.

The silhouette may be determined by an edge detection method. For example, a volume rendered aortic root image may be segmented by image intensity thresholding. Gradients of the segmented pixels may be determined. A maximum gradient value may be assigned to border pixels (e.g., pixels with at least one neighboring background pixel). Edge pixels may be detected by a hysteresis thresholding, similar, to Canny edge detector, on the gradient values. Connected components with a small number of detected edge pixels are removed to arrive at the silhouette.

It should be understood that any target detection method may be used and that the present disclosure is not limited to exemplary embodiments described herein.

If no aortic root is detected in the image, a position of an instrument or other structure of interest may be detected (105). The 3D model may be overlaid relative to the detected position (106). The detected position may be a previously determined relative position, e.g., from block 104 of FIG. 1.

A machine learning method may be used detect and track the instrument (105), such as a pigtail catheter. In an exemplary case of a pigtail catheter, a classifier may be trained, which can determine how likely a pixel is to be at a center of a catheter tip. All pixels in the image may be tested and the pixel with a largest probability to be the catheter tip center is taken as a detection result. After detecting the instrument, e.g., the pigtail catheter tip, on a first image, the detected position is propagated to a subsequent frame. The classifier may then be applied to detect a position around initial propagated position. The classification around initial propagated position is similar to catheter tip detection on the first frame, but the searching region may be reduced. A detection/tracking result may be highlighted in the overlay by drawing a bounding box of the instrument.

It should be understood that any instrument detection method may be used and that the present disclosure is not limited to exemplary embodiments described herein.

If neither an aortic root nor an instrument/structure is detected in the image, the 3D model may be overlaid at the position (e.g., [x,y] coordinates) taken from a previous image (107). Alternatively, a position of the 3D model can be estimated by a motion model of the region of interest (108). For example, since the cardiac motion has a substantially regular periodic pattern, it is possible to predict the new position of the aortic model based on the current or previous position.

More particularly, cardiac motion can be learned for various parts of the aorta by 3D tracking of landmarks such as the pigtail catheter temporarily put at the target (e.g., aortic root). The 3D motion estimated from tracking can be a combination of cardiac and breathing motion, and is further parameterized to provide an independent model for cardiac and breathing motion. Alternatively, cardiac motion may be isolated by ECG gating, and a breathing motion model may be built from the ECG gated tracking. The correlation motion model may also be learned for the relationship between the motions at different parts of the aorta at different cardiac and breathing phases to provide quantitative analysis about the influence of breathing and cardiac motion on the anatomical change of the aorta. The cardiac and respiratory phase can be obtained via a surrogate signal such as an ECG and spirometer, or an image-based method.

The method of FIG. 1 may be performed in real time.

In the case of interventional 3D imaging, such as DynaCT, live fluoro images and the 3D model are inherently initially registered because both images are acquired on the same system. The overlay dynamically adapts to the position of the X-ray detector, to detected movements of the patient and heart motion. Therefore, an acquisition step with contrast injection may be omitted as an initial or preliminary set of the medical procedure.

In the case of contrast-based registration, when a contrast agent washes out so that contrast-based registration is no longer viable, the method may return to a detection (e.g., blocks 101 or 105) and backtrack one or more frames.

Embodiments of the present disclosure may be extended to different clinical fields. For example, in a case where an anatomical structure of interest is only visible in live imaging under contrast injection, where the motion of the anatomical structure of interest can be derived from the motion of another visible structure or device, etc.

Referring to FIG. 2, in live imaging applications, the method may further include tracking the visible anatomical structure or device (201) and deriving the motion of the anatomical structure or device (202). The registrations may be of the live images to a 3D model and an overlay. That is, the methods of blocks 201 and 203 may be inserted in the flow of FIG. 1, for example, between blocks 101 and 102 of FIG. 1 or between blocks 105 and 106 of FIG. 1.

The method may further include detecting the contrast injection(s) (203); since a contrast injection may be performed at any time, this block may be inserted any where in the flow of FIG. 1 or 2. Contrast injections may be detected manually (e.g., by a technician noting a new injection) or detected by automatic methods.

Further, alternative image sources may be used. For live images, X-ray fluoro, ultrasound, endoscope cameras, etc., may be used. For overlaid model images, CT, MR, C-arm CT, ultrasounds, etc., may be used as 3D and 4D models.

FIG. 3A is an exemplary image overlay with contrast injection into an aortic root (301) and a catheter (302) prior to deploying a valve prosthesis (303). Also in FIG. 3A, landmarks of the aortic root (301) are visible, including commissures (304), the lowest points of the cusps (305), and a coronary ostia (306). FIG. 3B is an exemplary image overlay without contrast injection with a deployed valve prosthesis (303).

It is to be understood that embodiments of the present disclosure may be implemented in various forms of hardware, software, firmware, special purpose processors, or a combination thereof. In one embodiment, a software application program is tangibly embodied on a non-transitory computer-readable storage medium, such as a program storage device or non-transitory computer-readable storage medium, with an executable program stored thereon. The non-transitory computer-readable media comprises all computer-readable media, with the sole exception being a transitory, propagating signal. The application program may be uploaded to, and executed by, a machine comprising any suitable architecture.

Figure 4:
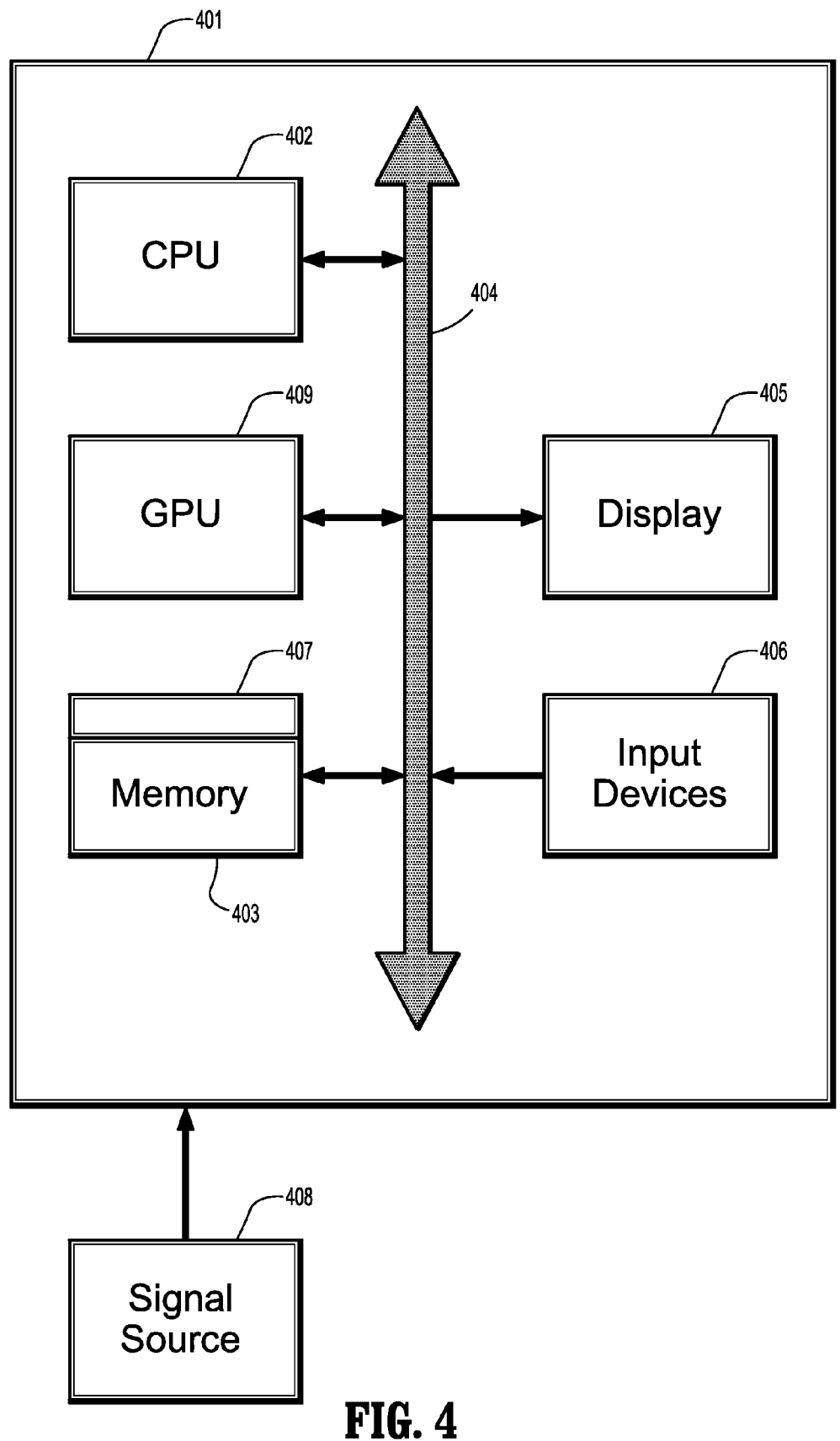
FIG. 4 is a diagram of a system for model registration with motion compensated overlays according to an embodiment of the present disclosure.

Referring to FIG. 4, according to an embodiment of the present disclosure, a computer system (block 401) for performing model registration with motion compensated overlays includes, inter alia, a CPU (block 402), a memory (block 403) and an input/output (I/O) interface (block 404). The computer system (block 401) is generally coupled through the I/O interface (block 404) to a display (block 405) and various input devices (block 406) such as a mouse, keyboard, medical scanners, power equipment, etc. The display (block 405) may be implemented to display the rules, e.g., as the rules evolve during evaluation, ranking and refinement or as an output set of rules. The support circuits can include circuits such as cache, power supplies, clock circuits, and a communications bus. The memory (block 403) can include random access memory (RAM), read only memory (ROM), disk drive, tape drive, etc., or a combination thereof. The present invention can be implemented as a module (block 407) of the CPU or a routine stored in memory (block 403) and executed by the CPU (block 402) to process input data (block 408). For example, the data may include image information from a camera, which may be stored to memory (block 403) As such the computer system (block 401) is a general purpose computer system that becomes a specific purpose computer system when executing the routine of the present disclosure. The computer system (block 401) may further include a GPU (block 409) for image processing.

The computer platform (block 401) also includes an operating system and micro instruction code. The various processes and functions described herein may either be part of the micro instruction code or part of the application program (or a combination thereof) which is executed via the operating system. In addition, various other peripheral devices may be connected to the computer platform such as an additional data storage device and a printing device.

It is to be further understood that, because some of the constituent system components and method steps depicted in the accompanying figures may be implemented in software, the actual connections between the system components (or the process steps) may differ depending upon the manner in which the system is programmed. Given the teachings of the present disclosure provided herein, one of ordinary skill in the related art will be able to contemplate these and similar implementations or configurations of the present disclosure.

Having described embodiments for model registration with motion compensated overlays, it is noted that modifications and variations can be made by persons skilled in the art in light of the above teachings. It is therefore to be understood that changes may be made in embodiments of the present disclosure that are within the scope and spirit thereof.

What is claimed is:

1. A method for generating a motion compensated overlay, comprising:
   receiving a 3D model of an aortic root shape;
   segmenting the received 3D model of the aortic root shape using intensity thresholding;
   determining gradients for the segmented 3D model;
   assigning a maximum gradient value to border pixels using the determined gradients;
   detecting edge pixels from the segmented 3D model using the determined gradients and the assigned maximum gradient values;
   producing a silhouette model of the aortic root shape by removing connected components having a small number of detected edge pixels from the segmented 3D model;
   capturing an image depicting an aortic root and an instrument;
   determining whether the aortic root shape is visible in the image;
   registering the produced silhouette to the captured image upon determining that the aortic root shape is visible in the captured image; and
   combining the produced silhouette with the captured image according to a registration to produce an overlay image.

2. The method of claim 1, further comprising determining a relative position of the model of the aortic root shape and the instrument in the overlay image.

3. The method of claim 2, wherein the method further comprises:
   tracking one of the aortic root shape and the instrument in the image; and
   deriving a motion of the aortic root shape or the instrument from the tracking,
   wherein the registration of the produced silhouette to the image is performed in real-time.

4. The method of claim 1, wherein the image is of a live fluoroscopic scene.

5. The method of claim 4, further comprising detecting a contrast agent in the live fluoroscopic scene.

6. The method of claim 1, wherein a computer program product embodies instructions executable by a processor to perform the method for displaying a motion compensated overlay.

7. A system for performing a method of displaying a motion compensated overlay, the system comprising:
   a processor configured to determine an overlay including a produced silhouette of a 3D model of an aortic root shape and an image, the processor executing instructions to perform a method comprising:
   receiving the 3D model of the aortic root shape;
   segmenting the received 3D model of the aortic root shape using intensity thresholding;
   determining gradients for the segmented 3D model;
   assigning a maximum gradient value to border pixels using the determined gradients;
   detecting edge pixels from the segmented 3D model using the determined gradients and the assigned maximum gradient values;
   producing a silhouette model of the aortic root shape by removing connected components having a small number of detected edge pixels from the segmented 3D model;
   capturing the image depicting an aortic root and an instrument;
   determining whether the aortic root shape is visible in the image;
   registering the produced silhouette to the captured image upon determining that the aortic root shape is visible in the captured image; and
   combining the produced silhouette with the captured image according to a registration to produce an overlay image; and
   a memory configured to store the overlay image.

8. The system of claim 7, wherein the method further comprises determining a relative position of the model of the aortic root shape and the instrument in the overlay image.

9. The system of claim 7, wherein the image is of a live fluoroscopic scene.

10. The system of claim 7, wherein the method further comprises:
    tracking one of the aortic root shape and the instrument in the image; and
    deriving a motion of the aortic root shape or the instrument from the tracking,
    wherein the registration of the produced silhouette to the image is performed in real-time by the system.

* * * * *